(12) United States Patent
Rapoza

(10) Patent No.: US 9,642,928 B1
(45) Date of Patent: May 9, 2017

(54) PERSONALIZED AIR FRESHENER SYSTEM

(71) Applicant: Nelson Rapoza, Acushnet, MA (US)

(72) Inventor: Nelson Rapoza, Acushnet, MA (US)

( * ) Notice: Subject to any disclaimer, the term of this patent is extended or adjusted under 35 U.S.C. 154(b) by 0 days.

(21) Appl. No.: 15/092,879

(22) Filed: Apr. 7, 2016

Related U.S. Application Data

(60) Provisional application No. 62/253,389, filed on Nov. 10, 2015.

(51) Int. Cl.
*A61L 9/04* (2006.01)
*A61L 9/12* (2006.01)
*A61L 9/03* (2006.01)
*A01M 1/20* (2006.01)

(52) U.S. Cl.
CPC ............. *A61L 9/12* (2013.01); *A01M 1/2055* (2013.01); *A61L 9/03* (2013.01); *A61L 2209/131* (2013.01); *A61L 2209/15* (2013.01)

(58) Field of Classification Search
CPC .. A61L 9/12; A61L 2209/131; A61L 2209/15; A61L 9/03; A01M 1/2055
USPC .................. 239/34, 36, 54, 55, 57, 211, 289
See application file for complete search history.

(56) References Cited

U.S. PATENT DOCUMENTS

| | | | | |
|---|---|---|---|---|
| 5,383,598 A | * | 1/1995 | Styles | A61L 9/12 239/34 |
| 5,678,763 A | * | 10/1997 | Scheuer | A61L 9/12 239/54 |
| 5,961,043 A | * | 10/1999 | Samuelson | A01M 1/2044 239/57 |
| 6,557,778 B1 | * | 5/2003 | Shiffler | A01M 1/2055 239/54 |
| 7,926,735 B1 | * | 4/2011 | Mobley | A61L 9/04 239/55 |

* cited by examiner

*Primary Examiner* — Steven J Ganey

(57) ABSTRACT

An air-freshening body is held within a transparent air-permeable enclosure, and can be customized through the application of a user-customized cover. The enclosure included a tab and a pocket; the pocket houses the air-freshening body and is accessible through a slit. Eyelets are traverse through the enclosure, allowing for string to be looped through the formed holes in order to hang the enclosure from an object or support. The eyelets are arranged to allow the enclosure to be held in a vertical, horizontal, or diagonal position. To help secure the air-freshening body within the pocket, a user-actuated seal is provided. The user-actuated seal closes the slit to hold the air-freshening body in place. A desired image can be printed onto an adhesive-backed sheet. The adhesive-backed sheet can then be applies to the air-freshening body in order to serve as the user-customizable cover.

12 Claims, 11 Drawing Sheets

PERSONALIZED AIR FRESHENER SYSTEM

The current application claims a priority to the U.S. Provisional Patent application Ser. No. 62/253,389 filed on Nov. 10, 2015.

FIELD OF THE INVENTION

The present invention relates generally to a customizable kit for air fresheners that allows a user to create a personalized air freshener.

BACKGROUND OF THE INVENTION

Offensive smells exist in the environment of humans. These smells can be generated by a wide variety of things such as the use of a toilet, dirty gym clothes, lack of personal hygiene, or a full garbage can. Whenever an offensive smell is found in an area, the usual course of action of occupants of that area is to find a way to eliminate that offensive smell. A myriad of air freshening technologies have been developed which offer people a way to eliminate, or at the very least, cover up offensive smells and make an area more comfortable for occupants. One area that is often subject to offensive smells is the interior of a car or other vehicle. The interior of a car is very small and must sometimes carry things that generate offensive smells such as garbage, dirty clothes, and people with poor hygiene. To combat this, the most common form of car air freshener is often used. Most car air fresheners are comprised simply of a scent impregnated material which is hung from somewhere in the car, most commonly the rear view mirror. These air fresheners are cheap and effective and as such are widely used by consumers, especially in public transportation such as busses and taxis. These air fresheners, though cheap and effective, suffer from one major flaw in particular; they are not customizable. This type of car air freshener hangs in full view of vehicle occupants, and as such, it is desirable to have an air freshener that is decorative and pleasing to the driver of the vehicle. It is an object of the present invention to solve the customizability issue by introducing a kit and method that allows a user to create an air freshener bearing any image of their choosing that can be printed from a computer.

DETAIL DESCRIPTIONS OF THE INVENTION

All illustrations of the drawings are for the purpose of describing selected versions of the present invention and are not intended to limit the scope of the present invention.

Figure 1:
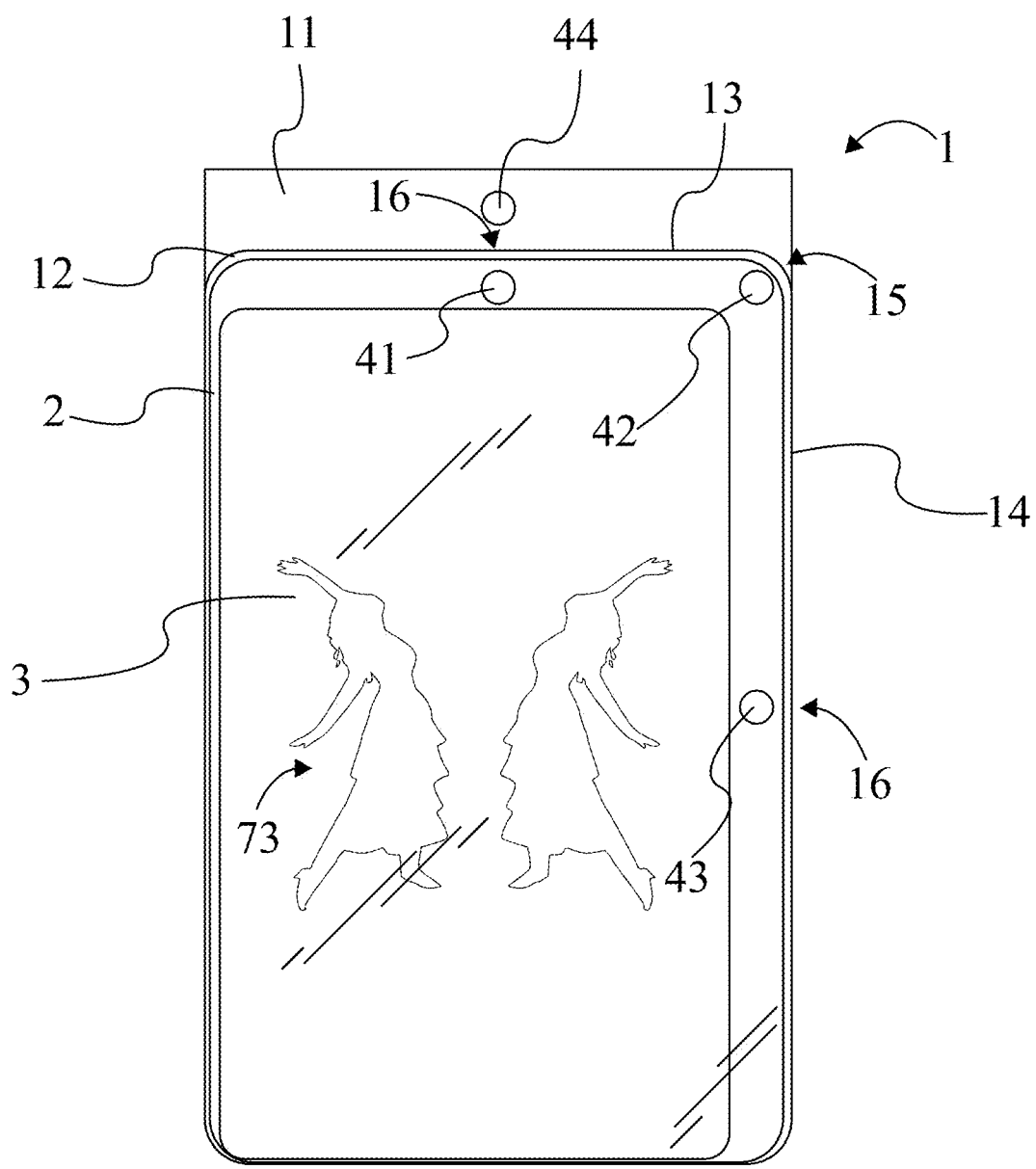
FIG. 1 is a front view illustration showing the present invention with a user-customized cover.

The present invention provides an aromatic device which is easily personalized by a user. The present invention comprises an transparent air-permeable enclosure 1, an air-freshening body 2, a user-customized cover 3, a plurality of eyelets 4, and a slit 5. The transparent air-permeable enclosure 1 serves as a housing for the air-freshening body 2. The user-customized cover 3 is applied to the air-freshening body 2 and allows for individuals to apply desired graphics (e.g. pictures) to the air-freshening body 2. The plurality of eyelets 4 allows for string or similar supports to be threaded through the enclosure. The threaded string can then be used to hang the enclosure from an external mount, for example a hook, nail, doorknob, or other item. The slit 5 provides access to the interior of the transparent air-permeable enclosure 1; mores specifically, the air-freshening body 2 can be inserted and removed from the transparent air-permeable enclosure 1 by means of the slit 5. FIG. 1 shows the present invention with an example potential graphic on the user-customized cover 3.

In elaboration of the above, the transparent air-permeable enclosure 1 comprises a tab 11 and a pocket 12, with the tab 11 being adjacently connected to the pocket 12. The tab 11 serves as a handle for the pocket 12 as well as a potential location for one of the plurality of eyelets 4 (as later described). The pocket 12 itself holds the air-freshening body 2. Resultantly, the air-freshening body 2 is positioned within the pocket 12. As referenced earlier, the interior of the pocket 12 is accessible by the slit 5, with the slit 5 traversing into the pocket 12. The transparent air-permeable enclosure 1 (including stored air-freshening body 2) can be hung from a supporting structure thanks to the eyelets 4 which can receive string, hooks, or other supports. The plurality of eyelets 4 allows for the transparent air-permeable enclosure 1 to be held in a variety of orientations, as elaborated upon below. Illustrations of such are provided via FIG. 2-FIG. 4.

The pocket 12, along which some of the eyelets 4 are positioned, comprises an upper edge 13 and a side edge 14. The plurality of eyelets 4 comprises a first eyelet 41, a second eyelet 42, and a third eyelet 43 which are positioned along the perimeter of the pocket 12. More specifically, the first eyelet 41, second eyelet 42, and third eyelet 43 are positioned along the upper edge 13 and the side edge 14, forming an "L" shape. The first eyelet 41 is centered at the top of the pocket 12; that is, the first eyelet 41 is positioned adjacent to a midpoint 16 of the upper edge 13. The second eyelet 42 is positioned at a top corner of the pocket 12; that is, the second eyelet 42 is positioned adjacent to an intersection 15 of the upper edge 13 and the side edge 14. The third eyelet 43 is centered at the side of the pocket 12; that is, the third eyelet 43 is positioned adjacent to a midpoint 16 of the side edge 14. As illustrated in FIG. 1-FIG. 4, a first line coincident with the first eyelet 41 and the second eyelet 42 is perpendicular to a second line coincident with the second eyelet 42 and the third eyelet 43.

Figure 2:
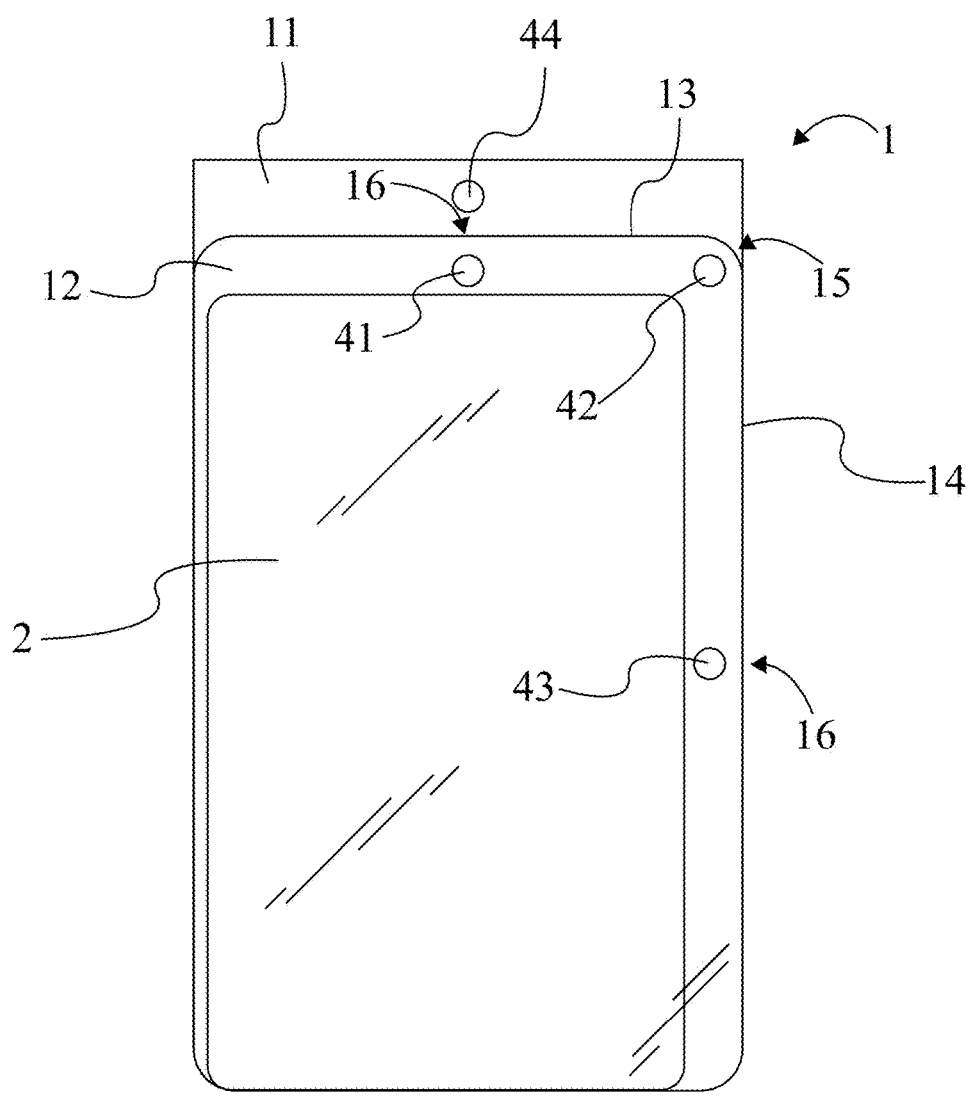
FIG. 2 is a front view illustration showing the present invention in a vertical orientation.
Figure 3:
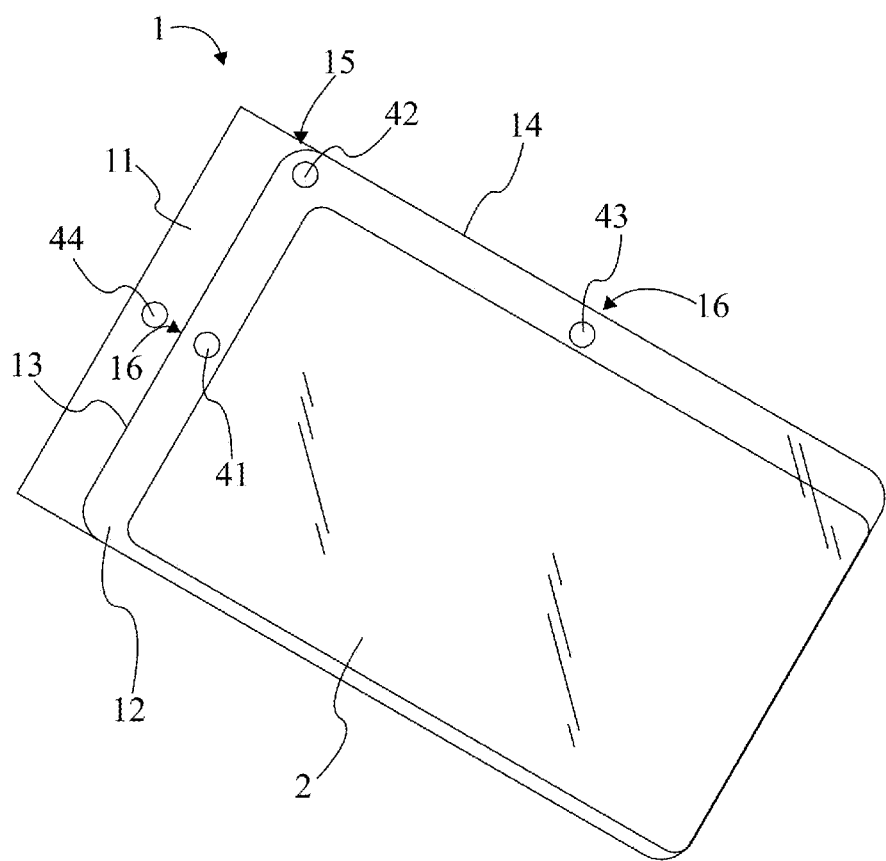
FIG. 3 is a front view illustration showing the present invention in a horizontal orientation.
Figure 4:
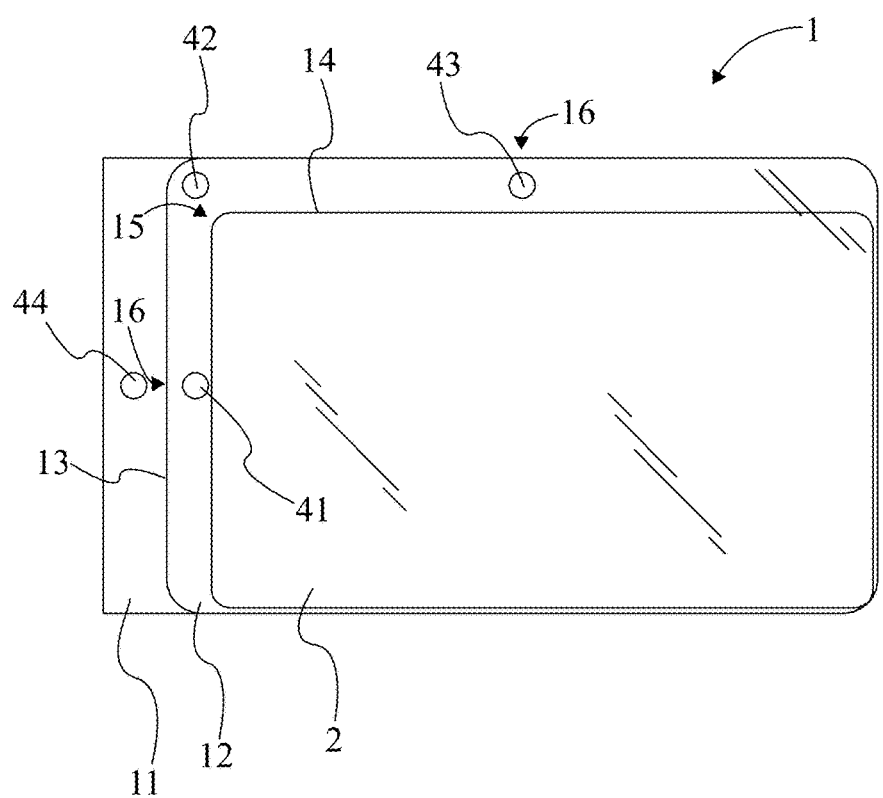
FIG. 4 is a front view illustration showing the present invention in a diagonal orientation.

By providing the first eyelet 41, second eyelet 42, and third eyelet 43 in such a configuration, a user is afforded the opportunity to suspend the pocket 12 (and thus transparent air-permeable enclosure 1) in multiple orientations. For example, a vertical (often referred to as "portrait") orientation is possible by threading a string or similar support from the first eyelet 41 and the second eyelet 42, i.e. along the upper edge 13. An example of a portrait orientation is shown in FIG. 2. Alternatively, a horizontal (often referred to as a "landscape") orientation is possible by supporting the pocket 12 from the second eyelet 42 and the third eyelet 43, i.e. along the side edge 14. An example of a horizontal orientation is shown in FIG. 3. It is also possible to create a diagonal orientation by supporting the pocket 12 from the first eyelet 41 and the third eyelet 43, i.e. along the upper edge 13 and the side edge 14. An example of a diagonal orientation is shown in FIG. 4. Of course, the present invention is not restricted to three eyelets for the pocket 12; in other embodiment additional eyelets may be positioned along the pocket 12 to enable further orientations, e.g. increasing or decreasing the possible slops of a diagonal orientation.

Potentially, in one embodiment, the first eyelet 41, second eyelet 42 and third eyelet 43 traverse through the air-freshening body 2 in addition to the transparent air-permeable enclosure 1. Otherwise, a gap would have to be provided between the edge of the air-freshening body 2 and the edge of the pocket 12 to ensure there is enough room for a string to be placed through the pocket 12 without being interfered by the air-freshening body 2. Such a gap is certainly possible within the scope of the present invention, but it may be considered unsightly or an efficient use of space; traversing the eyelets through the air-freshening body 2 alleviates such concerns by allowing for string to pass through the air-freshening body 2 and negating the need for a gap. Preferably, the eyelets are positioned around the perimeter of the air-freshening body 2, as they could otherwise interrupt the user-customized cover 3 which is attached to the air-freshening body 2. The positioning of these eyelets is shown I FIG. 1-FIG. 4.

Potentially, one of the eyelets 4 may traverse through the tab 11. In such an embodiment, the plurality of eyelets 4 comprises a tab eyelet 44. It is this tab eyelet 44 that traverses through the tab 11, preferably in a central position for optimal support. This tab eyelet 44 can be used as an additional support or an individual support. For example, a string could be threaded through the tab eyelet 44 and the aforementioned third eyelet 43. Alternatively, the tab eyelet 44 can receive the arm of a retail display, allowing the present invention easily be stored and shown in a retail environment. Furthermore, positioning of the tab eyelet 44 may be adjusted as desired by a manufacture. An embodiment including such is illustrated in FIG. 1-FIG. 4.

Combinations, substitutions, and alternations to the eyelets 4 described above are possible within the scope of the present invention. Ultimately, any implementation of eyelets (including alterations to shape and size) that allow the transparent air-permeable enclosure 1 to be supported from an external object are compatible with the present invention.

While the eyelets allow for the transparent air-permeable enclosure 1 to be hung from an object, the slit 5 provides access to the interior of the transparent air-permeable enclosure 1 and more specifically to the interior of the pocket 12. In different embodiments, the slit 5 may be placed at different parts of the pocket 12.

Figure 5:
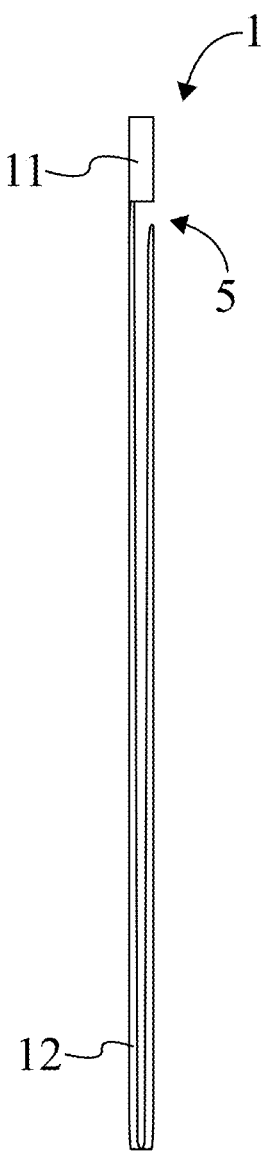
FIG. 5 is a side view illustration showing a top located slit of the present invention.
Figure 6:
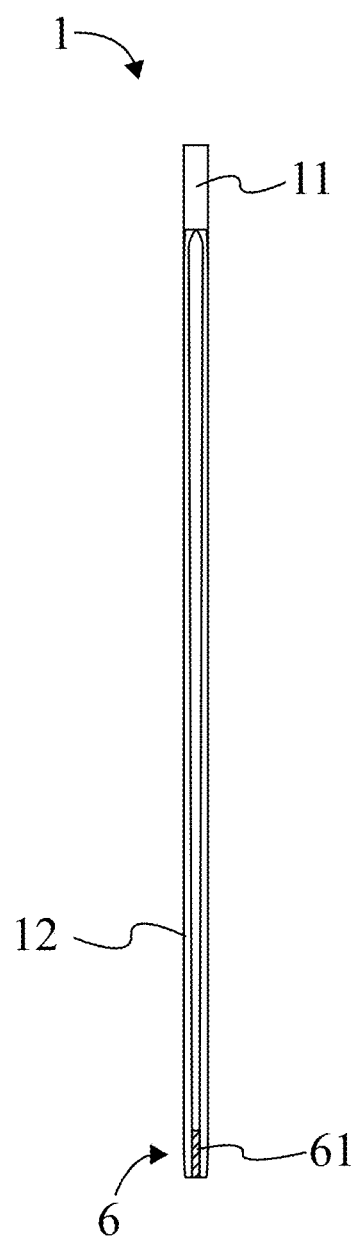
FIG. 6 is a side view illustration showing a bottom located slit with user-actuated seal of the present invention.

For example, in one embodiment the slit 5 is positioned adjacent to the tab 11. This embodiment allows for an air-freshening body 2 to easily be inserted from the top of the pocket 12. In another embodiment, the slit 5 may instead be positioned opposite the tab 11 across the pocket 12; in other words, the slit 5 may be positioned at the bottom of the pocket 12. The air-freshening body 2 can then be placed in the pocket 12 from the bottom. Potentially, in further embodiments side loading of the air-freshening body 2 may be enabled by placing the slit 5 at the side edge 14 of the pocket 12. An example of a slit 5 positioned at the top is provided through FIG. 5, while FIG. 6 illustrates a bottom-placed slit 5.

In some embodiments, it may be desirable or even necessary for a seal to be provided for the slit 5. For example, with a bottom slit 5 the air-freshening body 2 would fall out of the slit 5 is not closed. Resultantly, a user-actuated seal 6 is connected along the pocket 12, adjacent to the slit 5. This user-actuated seal 6 allows for a person to open and close the slit 5 in order to insert, remove, or secure an air-freshening body 2 within the pocket 12. Different embodiments of the present invention implement the user-actuated seal 6 in different ways, a few examples of which are described below.

In one embodiment, the user-actuated seal 6 comprises an adhesive strip 61. This adhesive strip 61 is positioned within the pocket 12, such that applying pressure to the adhesive strip 61 bonds the inside surfaces of the pocket 12. The bond created by the adhesive strip 61 is preferably strong enough to join said inside surfaces, but weak enough that a person can pull the inside surfaces in order to open the slit 5. If the bond created by the adhesive strip 61 were permanent, then a user would not be able to replace the air-freshening body 2 when it loses effectiveness; instead the user would have to throw away the transparent air-permeable enclosure 1 in addition to the air-freshening body 2, creating unnecessary additional waste. This embodiment is illustrated through FIG. 6.

In another embodiment, the user-actuated seal 6 comprises a flap 62. The flap 62 comprises a fixed edge 63 and a free edge 64; the free edge 64 is able to move independent of the pocket 12, while the fixed edge 63 serves as an axis of rotation. Effectively, the fixed edge 63 enables the flap 62 to act as a living hinge. The flap 62 itself is foldably connected to the pocket 12 along the slit 5, and thus the fixed edge 63 is positioned adjacent to the slit 5. The flap 62 can thus be folded to allow or prevent access to the pocket 12 by opening or blocking the slit 5.

Figure 7:
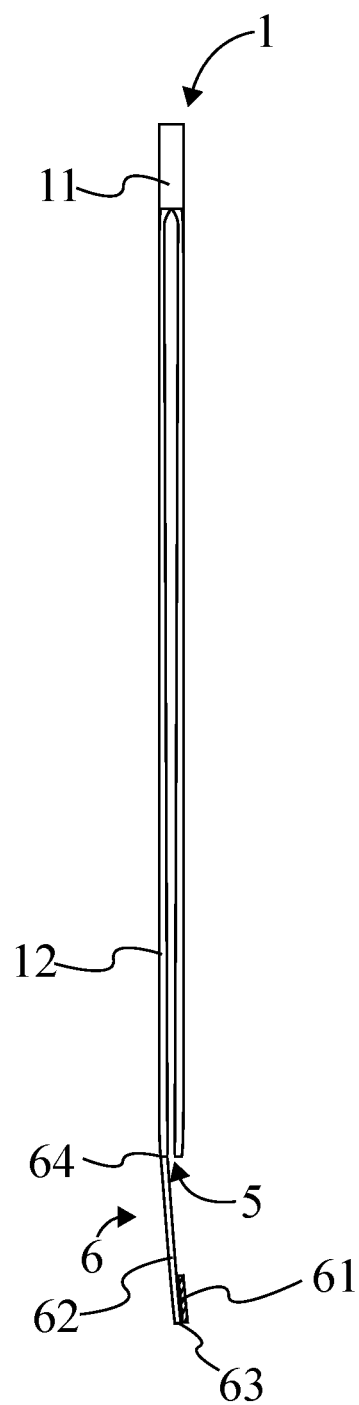
FIG. 7 is a side view illustration showing a flap style user-actuated seal of the present invention.
Figure 8:
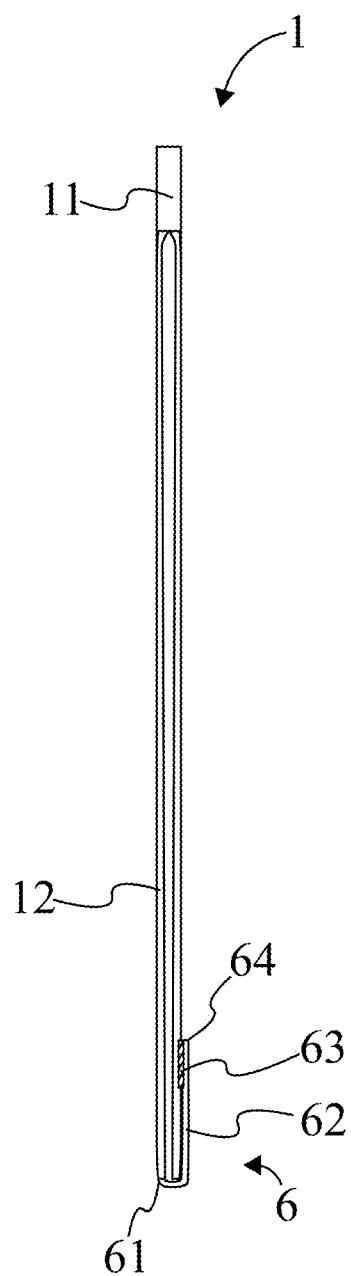
FIG. 8 is a side view illustration showing the flap style user-actuated seal in a closed position.

To help secure the flap 62, an adhesive strip 61 may be connected along the free edge 64. The adhesive strip 61 serves to attached the free edge 64 to the pocket 12 when the flap 62 is folded to a closed position and pressure is applied to the adhesive strip 61. As previously referenced, it is preferable that the bond created between the free edge 64 and the pocket 12 by the adhesive strip 61 is strong enough to stay in place but weak enough to allow a person to break the bond. This embodiment is shown via FIG. 7, which illustrated the flap 62 in an open position, and FIG. 8, which illustrates the flap 62 in a closed position.

These above examples of a user-actuated seal 6 are compatible with any placement of the slit 5. For example, while a slit 5 located at the top of the pocket 12 does not necessarily require a seal. It may still be combined with the, for example, adhesive strip 61 or flap 62. Of course further components can be utilized for the user-actuated seal 6 within the scope of the present invention. Possibilities include, but are not limited to, snap fasteners, magnets, hook-and-loop fasteners, zippers, and so on.

The present invention, beyond providing an transparent air-permeable enclosure 1 for an air-freshening body 2, allows for a user to personalize the air-freshening body 2 by means of a user-customized cover 3. More specifically, the present invention allows a user to easily create said user-customized cover 3 and apply the user-customized cover 3 to the air-freshening body 2.

Figure 9:
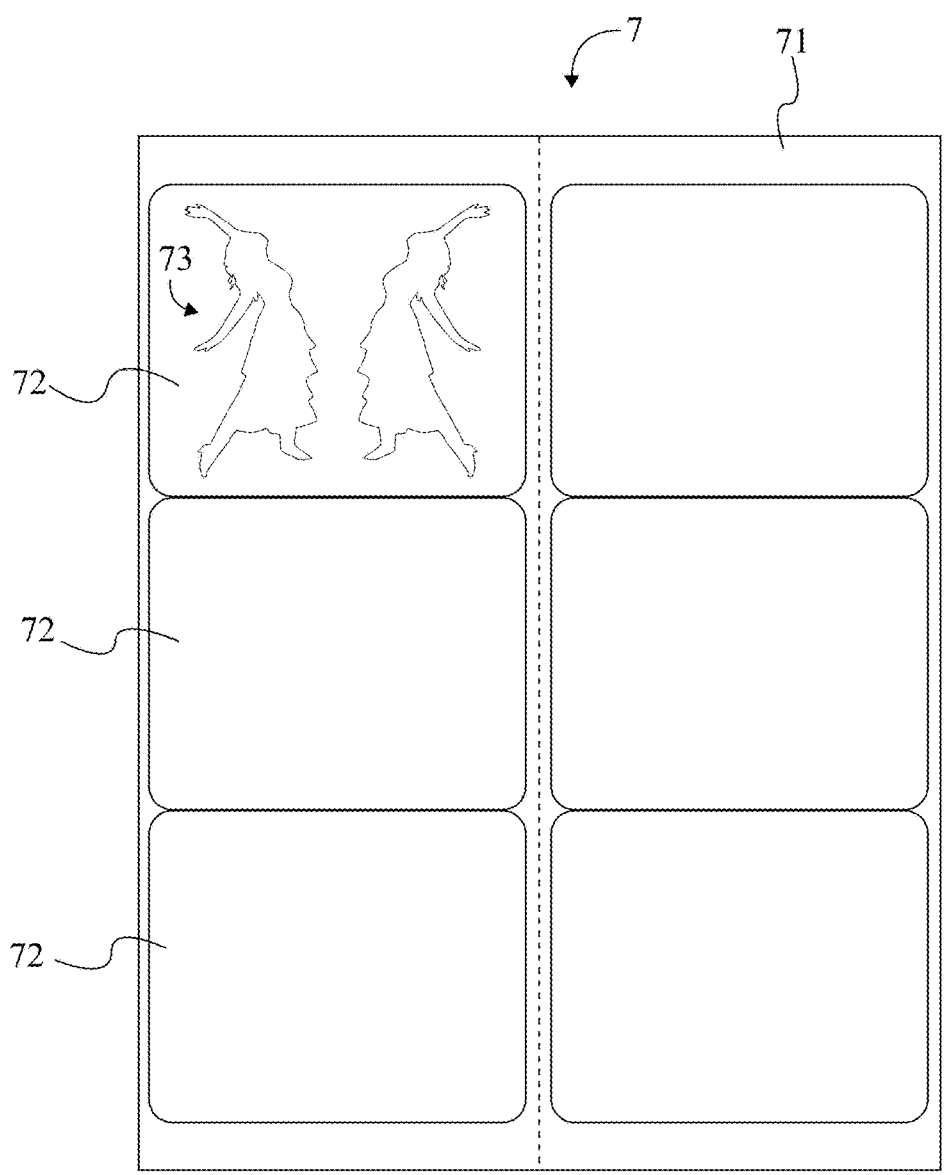
FIG. 9 is a top plan view illustration showing a paper membrane with printed graphics of the present invention.
Figure 10:
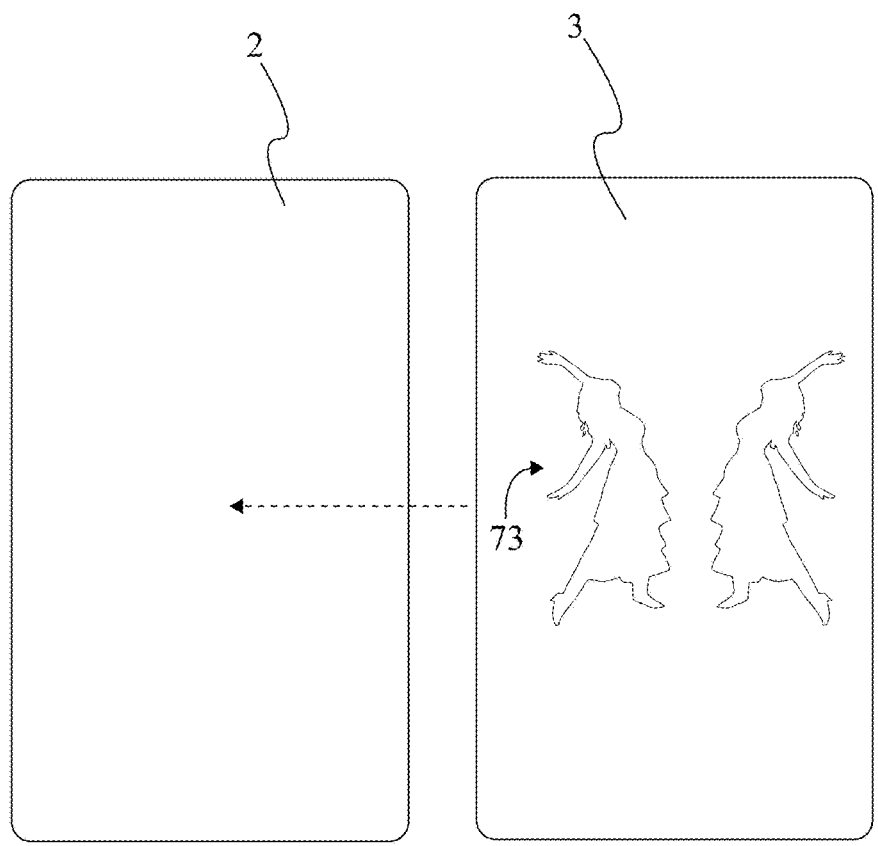
FIG. 10 is a top plan view showing a user-customized which is to be placed on an air-freshening body.
Figure 11:
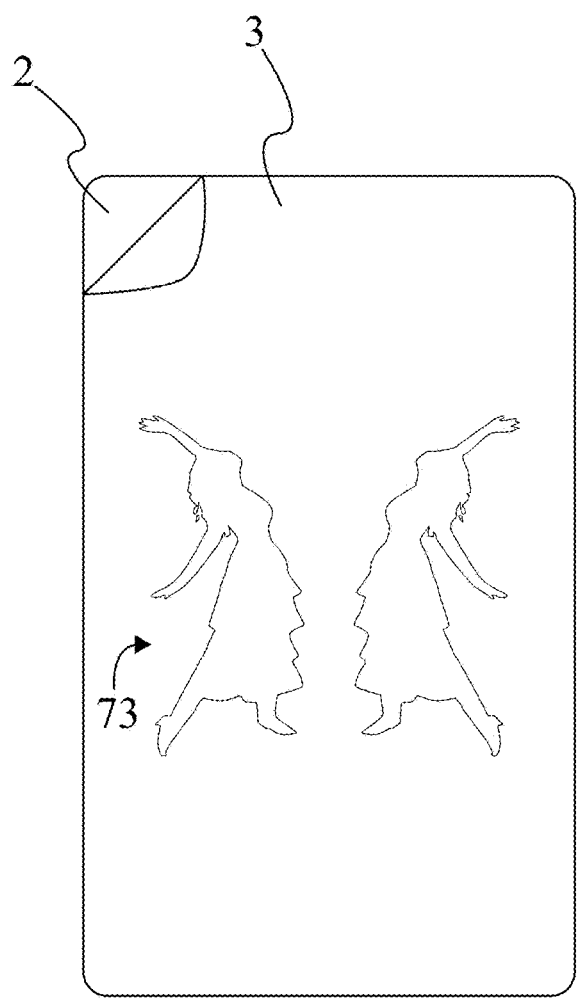
FIG. 11 is a top plan view showing an user-customized cover placed onto an air-freshening body.

To this end, a paper membrane 7 is utilized, with the paper membrane 7 preferably compatible with standard home and office printers. Generally, this requires a paper membrane 7 with dimensions of 8.5 inches by 11 inches, though some printers allow for variable sizes of paper. The paper membrane 7 comprises a release liner 71 and a plurality of adhesive-backed sheets 72. The plurality of adhesive-backed sheets 72 is attached to the release liner 71. This allows for any user-selected graphic 73 to easily be printed to the plurality of adhesive-backed sheets 72 by feeding the paper membrane 7 through a printer. The release liner 71 then allows one or more of the adhesive-backed sheets 72 to easily be removed. Once removed, an adhesive-backed sheet 72 can be applies to the air-freshening body 2, effectively becoming the user-customized cover 3. By this means, a user is able to obtain air-freshening bodies 2 with customized graphics without having to use specialized equipment or services; the entire process of creating and applying the user-customized cover 3 can be carried out within one's home with a home printer. An example process of doing such follows. The paper membrane 7 is shown in FIG. 9 while the process of applying the user-customized cover 3 to the air-freshening body 2 is shown in FIG. 10 and FIG. 11.

First, the paper membrane 7 is inserted into a printer. It is noted that use of high quality papers and adjustment of printer setting may be desirable to obtain optimal image quality. Next, the desired image is printed from a computer onto the paper membrane 7, more specifically onto the one or more of the plurality of adhesive-backed sheets 72. Third, the air-freshening body 2 is removed from its packaging (if any). Fourth, the adhesive-backed sheet 72 onto which the image was printed is removed from the release liner 71. Following this, the adhesive-backed sheet 72 is applied to the air-freshening body 2 to serve as the user-customized cover 3. The previous two steps can be repeated in order to attach a second user-customized cover 3 on an opposite face of the air-freshening body 2, resulting in the air-freshening body 2 being fully adorned. Once the user-customized cover 3 has been applied, the air-freshening body 2 can be placed within the pocket 12 through the slit 5. If a user-actuated seal 6 is included, it is then engaged to close the slit 5. Finally, string is inserted through two of the eyelets 4, forming a closed loop. The present invention is thus ready for use.

It is noted that while the above provides an example process, several steps may be performed in different orders. Additionally, steps may be omitted, substituted, or added while remaining within the scope of the present invention.

Overall, the present invention provides consumers with a great deal of flexibility. Users are able to display the transparent air-permeable enclosure 1 and air-freshening body 2 in a variety of orientations as desired. Further, a the user-customized cover 3 allows for a graphic (e.g. image or text) to be added to the air-freshening body 2 without requiring third party services. Another benefit is the ability to easily switch the air-freshening body 2. This reduces waste, as the transparent air-permeable enclosure 1 is reusable. The ability to swap out the air-freshening body 2 also allows for the user-customized cover 3 to easily be changed; as an example, during summer a user might use the logo of their favorited baseball team for the user-customized cover 3, while they might switch it to the logo of their favorite basketball team during winter.

Although the invention has been explained in relation to its preferred embodiment, it is to be understood that many other possible modifications and variations can be made without departing from the spirit and scope of the invention as hereinafter claimed.

What is claimed is:

1. A personalized air freshener system comprises:
an transparent air-permeable enclosure;
an air-freshening body;
a user-customized cover;
a plurality of eyelets;
a slit;
the transparent air-permeable enclosure comprises a tab and a pocket;
the user-customized cover being connected across the air-freshening body;
the tab being adjacently connected to the pocket;
the air-freshening body being positioned within the pocket;
the plurality of eyelets traversing through the enclosure;
the slit traversing into the pocket;
the plurality of eyelets comprises a tab eyelet;
the tab eyelet being centrally positioned on the tab;
a paper membrane;
the paper membrane comprises a release liner and a plurality of adhesive-backed sheets; and
the plurality of adhesive-backed sheets being attached to the release liner.

2. The personalized air freshener system as claimed in claim 1 comprises:
the pocket comprises an upper edge and a side edge;
the plurality of eyelets comprises a first eyelet, a second eyelet, and a third eyelet;
the first eyelet, the second eyelet, and the third eyelet being perimetrically positioned along the pocket;
the first eyelet being positioned adjacent to a midpoint of the upper edge;
the second eyelet being positioned adjacent to an intersection between the upper edge and the side edge; and
the third eyelet being positioned adjacent to a midpoint of the side edge.

3. The personalized air freshener system as claimed in claim 2 comprises:
the first eyelet, the second eyelet, and the third eyelet each traversing through the air-freshening body.

4. The personalized air freshener system as claimed in claim 1 comprises:
the slit being positioned adjacent to the tab.

5. The personalized air freshener system as claimed in claim 1 comprises:
the slit being positioned opposite the tab across the pocket.

6. The personalized air freshener system as claimed in claim 1 comprises:
a user-actuated seal; and
the user-actuated seal being connected along the pocket adjacent to the slit.

7. The personalized air freshener system as claimed in claim 6, wherein the slit is closed by the user-actuated seal.

8. The personalized air freshener system as claimed in claim 6 comprises;
the user-actuated seal comprises an adhesive strip; and
the adhesive strip being positioned within the pocket.

9. The personalized air freshener system as claimed in claim 1 comprises:
the user actuated seal being a flap;
the flap comprises a fixed edge;
the flap being foldably connected to the pocket along the slit; and
the fixed edge being positioned adjacent to the slit.

10. The personalized air freshener system as claimed in claim 9 comprises:
- an adhesive strip;
- the flap further comprises a free edge;
- the free edge being positioned opposite the slit across the flap;
- the adhesive strip being connected along the free edge; and
- the free edge being attached to the pocket by the adhesive strip.

11. The personalized air freshener system as claimed in claim 1, wherein a user-selected graphic is printed onto each of the plurality of adhesive-backed sheets.

12. The personalized air freshener system as claimed in claim 1 comprises;
- the user-customized cover being one of the plurality of adhesive-backed sheets, wherein one of the plurality of adhesive-backed sheets is removed from the release liner and applied to the air-freshening body.

\* \* \* \* \*